United States Patent [19]

Iwanami et al.

[11] Patent Number: 4,581,353
[45] Date of Patent: Apr. 8, 1986

[54] CEPHALOSPORIN DERIVATIVE AND PHARMACEUTICAL COMPOSITION

[75] Inventors: Masaru Iwanami, Kanagawa; Akio Koda, Tokyo; Yukiyasu Murakami, Saitama, all of Japan

[73] Assignee: Yamanouchi Pharmaceutical Co., Ltd., Tokyo, Japan

[21] Appl. No.: 628,971

[22] Filed: Jul. 11, 1984

Related U.S. Application Data

[63] Continuation of Ser. No. 461,444, Jan. 27, 1983, abandoned, which is a continuation of Ser. No. 277,046, Jun. 24, 1981, abandoned, which is a continuation of Ser. No. 154,364, May 29, 1980, abandoned.

[30] Foreign Application Priority Data

Jun. 7, 1979 [JP] Japan .................................. 54-71595
Mar. 10, 1980 [JP] Japan .................................. 55-30019

[51] Int. Cl.$^4$ .................. C07D 501/36; A61K 31/545
[52] U.S. Cl. ..................................... 514/206; 544/21; 544/27
[58] Field of Search ............................. 544/21, 22, 16; 514/206

[56] References Cited

U.S. PATENT DOCUMENTS 4,098,888  7/1978  Ochiai et al. ........................ 544/27
4,278,671  7/1981  Ochiai et al. ........................ 544/22
4,440,766  4/1981  Kamiya et al. ....................... 544/27

Primary Examiner—Nicholas S. Rizzo
Attorney, Agent, or Firm—Burgess, Ryan & Wayne

[57] ABSTRACT

A cephalosporin derivative of the formula

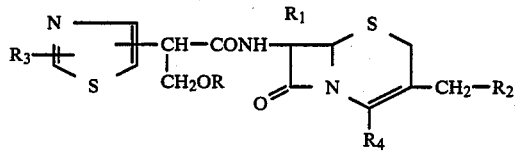

wherein R is a hydrogen atom, a lower alkyl group which may have been substituted or a carbamoyl group which may have been substituted; $R_1$ is hydrogen atom or a methoxy group; $R_2$ is a hydrogen atom, an acyloxy group, or a nitrogen-containing 5-membered heterocyclic thio group which may have been substituted; $R_3$ is a free amino group or an amino group having a protective group; and $R_4$ is a free carboxy group or a carboxy group having a protective group or the salts thereof.

The compound of this invention has an excellent antibacterial activity against gram negative bacteria and gram positive bacteria.

3 Claims, No Drawings

CEPHALOSPORIN DERIVATIVE AND PHARMACEUTICAL COMPOSITION

CROSS-REFERENCE TO RELATED APPLICATIONS

This application is a continuation of application Ser. No. 461,444, filed Jan. 27, 1983, now abandoned, which is in turn a continuation of co-pending application Ser. No. 277,046, filed June 24, 1981, now abandoned which, in turn, is a continuation of application Ser. No. 154,364, filed May 19, 1980, now abandoned.

BACKGROUND OF THE INVENTION

1. Field of the Invention

This invention relates to cephalosporin compounds wherein a propionamido group having a free or substituted hydroxy group at the 3-position and a thiazolyl group at the 2-position is linked to the 7-position of the cephalosporin compound. The invention further relates to a process of producing the aforesaid compounds. The compounds of this invention shows an excellent antibacterial activity to gram negative bacteria and gram positive bacteria and hence are useful as antibacterial agents.

2. Description of the Prior Art

Various kinds of cephalosporin derivatives are known and the cephalosporins having a propionamido group in which the 3-position is substituted with a hydroxy group and the 2-position is substituted with a heterocyclic group, as a side chain acylamido group at the 7-position are disclosed in Japanese Pat. Publn. (Open for Public Inspection) Nos. 101,388/'78; 16,495/'79 and 36,286/'79. These cephalosporins disclosed above show somewhat an actibacterial activity against Bacillus subtilis which is a gram positive bacterium but the antibacterial spectrum is relatively restricted.

SUMMARY OF THE INVENTION

As the result of continuing the investigations on a series of the cephalosporin derivatives having a 3-hydroxy-2-heterocyclic ring-substituted propionamido group at the 7-position described above, the inventors have discovered that by converting the substituent at the 2-position of the propionamido group linked to the 7-position to an aminothiazole group, a series of novel cephalosporin derivatives showing a wide antibacterial activity not only against gram positive bacteria such as Bacillus subtilis to which the known compounds described above show an antibacterial activity but also against gram negative bacteria, that is, showing different antibacterial spectra is obtained. In other words, the applicable range of cephalosporin derivatives can be expanded upto pathogens by different kind of bacteria by the present invention.

Thus, according to this invention, there are provided cephalosporin derivatives represented by following general formula I

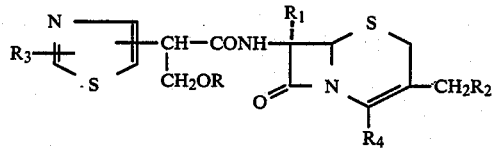

wherein R represents hydrogen atom, a lower alkyl group which may have been substituted, or a carbamoyl group which may have been substituted; $R_1$ represents a hydrogen atom or a methoxy group; $R_2$ represents a hydrogen atom, an acyloxy group, or a nitrogen-containing 5-membered heterocyclic thio group which may have been substituted; $R_3$ represents a free amino group or an amino group having a protective group; and $R_4$ represents a free carboxy group or a carboxy group having a protective group or the salts thereof.

DESCRIPTION OF THE PREFERRED EMBODIMENT

The compounds of this invention are shown by general formula I described above. In the general formula, the lower alkyl group shown by R means a straight chain or branched alkyl group having 1-4 carbon atoms, such as a methyl group, ethyl group, propyl group, isopropyl group, butyl group, isobutyl group, etc. The lower alkyl group may have a substituent such as halogen atom, nitro group, amino group, hydroxy group, etc. Also, R in the general formula represents a carbamoyl group which may have a lower alkyl group. As the acyloxy group shown by $R_2$, there are illustrated an acetoxy group, carbamoyloxy group, etc. The nitrogen-containing 5-membered heterocyclic group is a heterocyclic ring having at least one nitrogen atom and further, as the case may be, 1-3 hetero atoms such as an oxygen atom and sulfur atom and there are illustrated an oxadiazolyl group, thiazolyl group, triazolyl group, tetrazolyl group, oxazolyl group, thiazolyl group, isooxazolyl group, isothiazolyl group, etc. These heterocyclic groups each may have a substituent such as a methyl group, ethyl group, isopropyl group, dimethylaminoethyl group, carboxyethyl group, etc.

As the protective group for the amino group shown by $R_3$, protective groups usually used in the fields of cephalosporin and peptide chemistry are desirably used and examples of such protective groups are a trityl group, trimethylsilyl group, formyl group, propionyl group, methoxyacetyl group, benzyloxy group, carbonyl group, t-butoxycarbonyl group, phthaloyl group, etc.

As the protective group for the carboxy group shown by $R_4$, protective groups usually used as in the above case are desirably used and there are a methyl group, trimethylsilyl group, β-methylsulfonylethyl group, phenacyl group, p-methoxybenzyl group, nitrobenzyl group, benzyl group, benzhydryl group, t-butyl group, etc.

As the protective group for the groups shown by $R_3$ and $R_4$, a group which, when the compound is administered to a living body, accelerates absorption of the compound and is easily released in the body is used. Examples of such a protective group are an acetyl group or carboxy group for an acetyl group and phthalidyl group or pyvaloyloxymethyl group for a carboxy group.

The cephalosporin compounds of this invention shown by formula I have excellent antibacterial activity against various pathogens and are useful as antibacterial agents. The antibacterial activities of the compounds of formula I of this invention are shown in the following table in comparison with known compounds having similar structures.

TABLE 1

| | (antibacterial activity: minimum inhibiting concentration μg/ml) | | | | | | | | |
|---|---|---|---|---|---|---|---|---|---|
| | Compound of this invention | | | | | | | Known compound | |
| microorganism | Ex. 2 | Ex. 3 | Ex. 4 | Ex. 5 | Ex. 6 | Ex. 7 | Ex. 8 | A | B |
| *Bacillus subtilis* | 0.78 | 1.56 | 12.5 | 25 | 1.56 | 3.13 | 3.13 | 0.2 | 0.2 |
| *Staphylococcus aureus* | 1.56 | 3.13 | 12.5 | 25 | 1.56 | 6.25 | 3.13 | 0.78 | 0.2 |
| *Escherichia coli* NIHJ | ≦0.2 | 0.39 | 12.5 | 3.13 | ≦0.2 | 0.2 | ≦0.2 | 3.13 | 1.56 |
| *Shigella sonnei* | 0.39 | 0.78 | 25 | 12.5 | 1.56 | 3.13 | 0.39 | 3.13 | — |
| *Proteus mirabilis* | ≦0.2 | 1.56 | 12.5 | 6.25 | ≦0.2 | 0.39 | ≦0.2 | — | 25 |

Compound A:

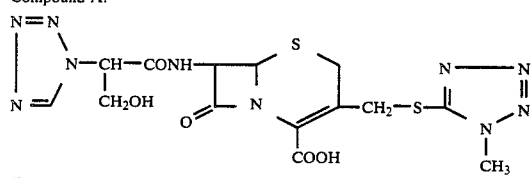

(Japanese published unexamined Pat. appln. No. 101388/1978)

Compound B:

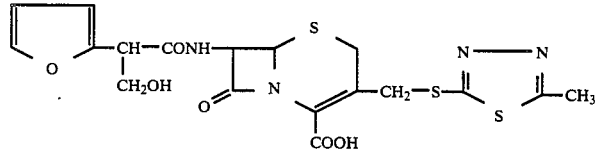

(Japanese published unexamined Pat. appln. No. 36286/1979)

The cephalosporin compounds of this invention shown by formula I are administered orally or parenterally as it is or in the form of the salt thereof for the treatment of diseases of human beings and animals. The doses of the cephalosporin compound depend on the condition, weight, age, etc., of a patient but the dose is usually 250-3000 mg per day for an adult, which is administered in 3-4 times a day.

The forms of the cophalosporin compounds suitable for administration are injections, tablets, capsules, syrups, etc., and they are prepared by novel procedures using excipients, preservatives, stabilizers, etc., used for preparing formulations of medicaments.

The cepahlosporin compounds of this invention shown by formula I are prepared by reacting the 7β-aminocephalosporin derivative shown by general formula II

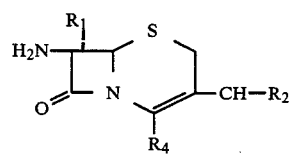

wherein $R_1$, $R_2$, and $R_4$ have the same significance as in general formula I or the reactive derivatives of the amino group and the thiazolylpropionic acid derivative shown by general formula III

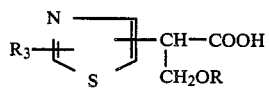

wherein R and $R_3$ have the same significance as in general formula I or the reactive derivative of the carboxy group thereof and, if necessary, releasing $R_3$ and/or $R_4$ from the product to convert the product into a salt thereof.

The 7β-aminocephalosporin derivatives shown by formula II or the reactive derivatives of the amino group thereof used as a starting material in the process can be also used in the form of the salt of sodium, potassium, triethylamine, etc., in the carboxy group at the 4-position thereof. Also, as the protective group for the carboxy group, a group which can convert the protected carboxy group to a free carboxy group under the conventional mild condition or increases the absorption of the cephalosporin compound in a body is desirably used.

The protective group for the amino group of the compounds of formula III which are another starting material in the process of this invention are also selected from protective groups ordinarily used in the fields of cephlosporin and peptide chemistry as the protective groups for the carboxy group of the compounds of formula II.

The reaction of a compound of formula II and a compound of formula III is usually performed in a solvent under cooling or at room temperature. Any solvents which do not have any adverse influences on the reaction may be used but tetrahydrofuran, acetone, chloroform, methanol, ethanol, methylene chloride, ethylene chloride, acetonitrile, ethyl acetate, ethyl formate, dimethylformamide, etc., are usually used. These solvents can be used solely or in the form a mixture.

As the reactive derivatives of the compound shown by formula III at the carboxy group thereof, there can be used the acid halides, mixed acid anhydrides, active esters, active amides, acid anhydrides, acid azides, etc.

When the reactive derivative of a compound of formula III at the carboxy group is in the form of the acid halide such as the acid chloride or the acid anhydride or a mixed acid anhydride, it is preferred to perform the reaction in the presence of a base. Examples of the base used in this case are organic bases such as triethylamine, pyridine, dimethylanilide, etc., and inorganic bases such as an alkali carbonate, an alkali hydrogencarbonate, etc.

When a compound of formula II is reacts with a compound of formula III in that both the amino group of the former compound and the carboxy group of the latter compound are in the free states, it is desirable to use a condensing agent such as N,N'-cyclohexylcarbodiimide, N,N'-diethylcarbodiimide, etc.

In the case of preparing a compound of the formula wherein R is hydrogen atom, a protective group for a hydroxy group usually used in the field of peptide chemistry, such as an acetyl group, etc., may be, if necessary, used and the protective group can be released by treating with a weak base.

The compounds of formula I wherein $R_3$ is a free amino group and/or $R_4$ is a free carboxy group can be prepared by releasing the protective group or groups by a conventional procedure. For example, a protective group for the amino group, such as a trityl group, t-butoxycarbonyl group, etc., can be released by an acid such as trifluoroacetic acid and a protective group such as the p-nitrobenzyloxycarbonyl group can be released by a catalytic reduction. A protective group for the carboxy group, such as a benzhydryl group, P-methoxybenzyl group, etc., can be easily released by an acid and a protective group such as a trimethylsilyl group can be easily released by the contact with water.

The compounds of formula I wherein $R_4$ is a free carboxy group thus obtained can be converted to pharmaceutically acceptable non-toxic salts thereof by conventional procedure. For example, the alkali metal salt of the compound is obtained by adding to the compound an n-butanol solution of an alkali metal 2-ethylhexanoate and then an organic solvent having a different solubility, such as ether, ethyl acetate, etc.; the organic base salt of the compound is obtained by adding to the base, an equivalent amount or slightly excessive amount of an organic base such as dicyclohexylamine, triethylamine, diethanolamine, arginine, lysine, etc.; and the ammonium salt of the compound is obtained by adding aqueous ammonia. Also, the compounds of formula I wherein $R_3$ is a free amino group can be converted into the pharmaceutically acceptable non-toxic salts thereof by conventional manner. For example, the salt of the compound is obtained by adding to the compound an equivalent amount or slightly excessive amount of an inorganic acid such as hydrochloric acid, phosphoric acid, sulfuric acid, etc., or an organic acid such as fumaric acid, maleic acid, malic acid, citric acid, benzoic acid, etc.

REFERENCE EXAMPLE 1

In 20 ml of dimethylsulfoxide was dissolved 4.14 g (0.01 mole) of methyl 2-tritylaminothiazol-4-yl acetate and after adding to the solution 413 mg of paraformaldehyde (80% purity) and then 30 mg of sodium methoxide, the mixture was stirred for 4 hours at room temperature.

To the reaction mixture was added 100 ml of ice-water and after neutralizing it by adding a small amount of hydrochloric acid, the reaction mixture was extracted once each time with 50 ml and 30 ml of ethyl acetate. The ethyl acetate extract was washed four times with water and after drying with anhydrous magnesium sulfate, the solvent was distilled off to provide 3.5 g of crude methyl 3-hydroxy-2-(2-tritylaminothiazol-4-yl)propionate. The product was purified by a silica gel column chromatography using a mixture of benzene and ethyl acetate in a 3:1 by volume ratio as an eluant.

(i) Elemental analysis for $C_{26}H_{24}N_2O_3S \cdot \frac{1}{2}CH_3COOC_2H_5$:

| | C (%) | H (%) | N (%) | S (%) |
|---|---|---|---|---|
| Calculated | 68.85 | 5.74 | 5.74 | 6.56 |
| Found | 68.31 | 5.45 | 5.72 | 6.25 |

(ii) Infrared absorption spectra (cm$^{-1}$): 1725 (ester), 3325 (OH).

(iii) Nuclear magnetic resonance spectra (CDCl$_3$):
ppm: 7.28 (15H (C$_6$H$_5$)$_3$C—),
6.48 (1H OH),

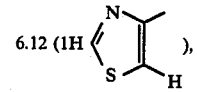
6.12 (1H), 3.66 (3H —COOCH$_3$), 3.87-3.4 (3H —C$\underline{H}$— ).
      |
      C$\underline{H_2}$O—

REFERENCE EXAMPLE 2

In 50 ml of dioxane was dissolved 2.0 g of the product obtained in Reference Example 1 and after adding thereto 5 ml of a 2N sodium hydroxide solution, the mixture was heated. After stirring the mixture for 30 minutes at 45° C., the solvent was distilled off under reduced pressure and the residue was acidified with hydrochloric acid and extracted with ethyl acetate. The organic layer was collected, washed with water and dried by anhydrous magnesium sulfate. The solvent was distilled off under reduced pressure and then acetonitrile was added to the residue to facilitate providing 700 mg of 3-hydroxy-2-(2-tritylaminothiazol-4-yl)propionic acid in crystalline form.

(i) Infrared absorption spectra (cm$^{-1}$): 1710 (—COOH).

(ii) Nuclear magnetic resonance spectra (d$_6$-DMSO):

ppm:
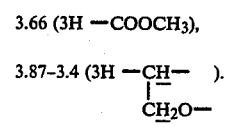
6.28 (1H)

3.4 (3H —C$\underline{H}$—)
     |
     C$\underline{H_2}$O

EXAMPLE 1

In 20 ml of tetrahydrofuran was dissolved 430 mg of 3-hydroxy-2-(2-tritylaminothiazol-4-yl)propionic acid and the solution was mixed with a solution prepared by dissolving 494 mg of 7β-amino-3-(1-methyltetrazol-5-yl)thiomethyl-Δ$^3$-cephem-4-carboxylic acid benzyhydryl ester in 30 ml of dichloromethane. To the mixed solution was added 206 mg of N,N'-dicyclohexylcarbodiimide and the resultant mixture was stirred for one hour. After distilling off the solvent from the reaction mixture under reduced pressure, 50 ml of dichloromethane was added to the residue and insoluble N,N'-dicyclohexylurea was filtered off. The filtrate was washed successively with acid, an aqueous sodium hydrogencarbonate solution, and water. The filtrate was dried by anhydrous magnesium sulfate, the residue was distilled off under reduced pressure, and after adding 30 ml of ether to the residue formed, the mixture was stirred for one hour. The powder formed was recovered by filtration and washed with ether to provide 680 mg of 7β-[3-hydroxy-2-(2-tritylaminothiazol-4-yl)propionamido]-3-(1-methyltetrazol-5-yl)thiomethyl-Δ³-cephem-4-carboxylic acid benzhydryl ester.

(i) Infrared absorption spectra (cm⁻¹, KBr):
1770 (lactum), 1710 (ester), 1660 (amide).
(ii) Nuclear magnetic resonance spectra (d₆-DMSO)

ppm:

6.10 (1H 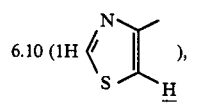), 5.67 (1H 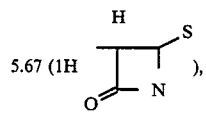), 5.06 (1H 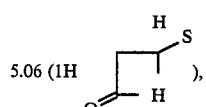), 4.24 (2H 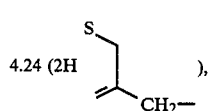), 3.83 (3H 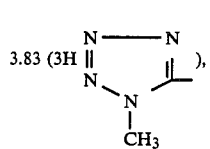), 3.7 (2H 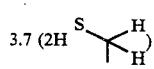)

3.5 (3H 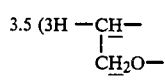)

EXAMPLE 2

In 20 ml of tetrahydrofuran was dissolved 430 mg of 3-hydroxy-2-(2-tritylaminothiazol-4-yl)propionic acid and the solution was mixed with a solution prepared by dissolving 494 mg of 7β-amino-3-(1-methyltetrazol-5-yl)thiomethyl-Δ³-cephem-4-carboxylic acid benzhydryl ester in 30 ml of dichloromethane. To the mixed solution was added 206 mg of N,N'-dicyclohexylcarbodiimide and the resultant mixture was stirred for one hour. After distilling off the solvent from the reaction mixture under reduced pressure, 50 ml of dichloromethane was added to the residue and insoluble N,N'-dicyclohexylurea was filtered off. The filtrate was washed successively with acid, an aqueous sodium hydrogencarbonate solution, and water. The filtrate was dried by anhydrous magnesium sulfate, the residue was distilled off under reduced pressure, and after adding 30 ml of ether to the residue formed, the mixture was stirred for one hour. The powder formed was recovered by filtration and washed with ether to provide 680 mg of 7β-[3-hydroxy-2-(2-tritylaminothiazol-4-yl)propionamido]-3-(1-methyltetrazol-5-yl)thiomethyl-Δ³-cephem-4-carboxylic acid benzhydryl ester.

In 10 ml of dichloromethane was dissolved the product thus obtained and after adding thereto 5 ml of trifluoroacetic acid and 1 ml of anisole, the mixture was stirred for one hour at room temperature. The reaction mixture was dried into solid under reduced pressure and ether was added to the residue to facilitate formation of a powder which was recovered by filtration. The powder was added to 10 ml of 10% formic acid followed by stirring for 30 minutes at 55° C. The reaction mixture thus obtained was dried into a solid under reduced pressure and the residue was washed with isopropyl ether and then purified by a column chromatography using Diaion HP 20 (trade name of ion-exchange resin, made by Mitsubishi Chemical Industries, Ltd.) to provide 7β-[2-(2-aminothiazol-4-yl)-3-hydroxypropionamido]-3-[(1-methyltetrazol-5-yl)thiomethyl]-Δ³-cephem-4-carboxylic acid.

(i) Infrared absorption spectra (cm⁻¹, KBr):
1760 (lactum), 1660 (amide).
(ii) Nuclear magnetic resonance spectra (d₆-DMSO)

ppm:

3.62 (2H 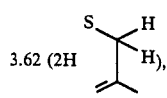), 3.68 (3H 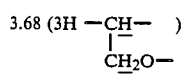)

3.91 (3H 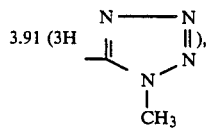), 4.28 (2H 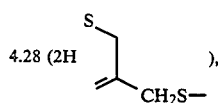), 5.0 (1H 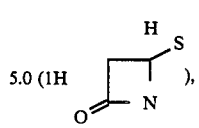), 5.63 (1H 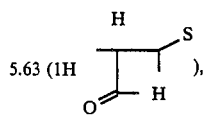), 6.19 (1H 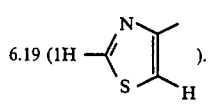).

EXAMPLE 3

In 10 ml of tetrahydrofuran was dissolved 295 mg of 3-hydroxy-2-(2-tritylaminothiazol-4-yl)propionic acid and after adding thereto 300 mg of 7β-aminocephlosporanic acid benzhydroyl ester and 141 mg of N,N'-dicyclohexylcarbodiimide, the mixture was stirred for 2 hours at room temperature. Then, the solvent was distilled off under reduced pressure and after adding 50 ml of dichloromethane to the residue, insoluble N,N'-dicyclohexylurea was filtered off. The filtrate was washed twice with water acidified with hydrochloric acid, once with an aqueous solution of sodium hydrogencarbonate, and once with an aqueous solution of sodium chloride. After drying the filtrate by anhydrous magnesium sulfate, the solvent was distilled off and ether was added to the residue to provide 440 mg of 3-acetoxymethyl-7β-[3-hydroxy-2-(2-tritylaminothiazol-4-yl)propionamido]-Δ³-cephem-4-carboxylic acid benzhydryl ester.

The ester was treated as in Example 2 to release the protective group and purified also using the same procedure as in Example 2 to provide 3-acetoxymethyl-7β-[2-(2-aminothiazol-4-yl)-3-hydroxypropionamido]-Δ³-cephem-4-carboxylic acid.

(i) Nuclear magnetic resonance spectra (d₆-DMSO)

ppm:

6.43 (1H 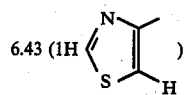 )

5.63 (1H 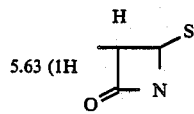 )

5.06 (1H 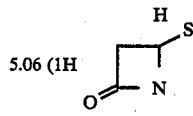 )

4.80 (2H 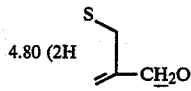 )

3.74 (3H —C$\underline{H}$— )
           |
          CH₂O 3.54 (2H 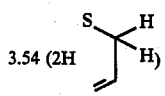 )

2.0 (3H —OCOC$\underline{H}_3$)

duced pressure, and isopropyl alcohol was added to the residue to form precipitates, which were recovered by filtration. The product was purified by a column chromatography using Diaion HP 20 (trade name) to provide 7β-[2-(2-aminothiazol-4-yl)-3-hydroxypropionamido]-3-methyl-Δ³-cephem-4-carboxylic acid.

(i) Infrared absorption spectrum (cm⁻¹, KBr):
    1755 (lactam).
(ii) Nuclear magnetic resonance spectra (d₆-DMSO)

ppm:

6.27 (1H 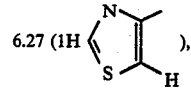 ), 5.54 (1H 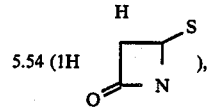 ), 4.90 (1H 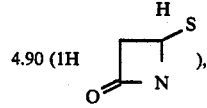 ), 3.70 (3H —C$\underline{H}$— ),
           |
          CH₂O—

3.66 (2H 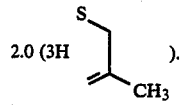 ), 2.0 (3H 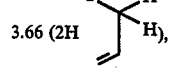 ).

EXAMPLE 4

In 20 ml of tetrahydrofuran were dissolved 430 mg of 3-hydroxy-2-(2-tritylaminothiazol-4-yl)propionic acid and 270 mg of 7β-aminodesacetoxycephalosporanic acid tert-butyl ester and after adding thereto 206 mg of N,N'-dicyclohexylcarbodiimide, the mixture was stirred for 2 hours at room temperature. The solvent was distilled off from the reaction mixture under reduced pressure and 60 ml of ethyl acetate was added to the residue. Insoluble N,N'-dicyclohexylurea thus formed was filtered off and the filtrate was washed with an aqueous hydrochloric acid solution, an aqueous solution of sodium hydrogencarbonate, and then water followed by drying with anhydrous magnesium sulfate. The solvent was distilled off under reduced pressure and the residue was dissolved in 2 ml of dichloromethane. After adding 4 ml of trifluoroacetic acid and 0.5 ml of anisole to the solution followed by stirring the mixture for 10 minutes at room temperature, 0.5 ml of water was added and the mixture was stirred vigorously. The solvent was distilled off from the reaction mixture under reduced pressure and ether was added to the residue to facilitate the formation of a powder, which was recovered by filtration. The powder was dissolved in 20 ml of ethanol, the insoluble materials which had formed were filtered off, the filtrate was adjusted to pH 4 by pyridine, the solvent was distilled off under re-

EXAMPLE 5

In 20 ml of tetrahydrofuran were dissolved 430 mg of 3-hydroxy-2-(2-tritylaminothiazol-4-yl)propionic acid and 524 mg of 7β-amino-7α-methoxy-3-(1-methyltetrazol-5-yl)thiomethyl-Δ³-cephem-4-carboxylic acid benzhydryl ester and after adding thereto 206 mg of N,N'-dicyclohexylcarbodiimide, the mixture was stirred for 3 hours at room temperature. The reaction mixture thus obtained was treated as in Example 1 to provide 620 mg of 7α-methoxy-3-(1-methyltetrazol-5-yl)thiomethyl-7β-[2-(2-tritylaminothiazol-4-yl)-3-hydroxypropionamido]-Δ³-cephem-4-carboxylic acid benzhydryl ester.

The ester was dissolved in 7 ml of dichloromethane and after adding thereto 5 ml of trifluoroacetic acid, the mixture was stirred for 10 minutes. The solvent was distilled off from the reaction mixture under reduced pressure and ether was added to the residue to form a powder, which was filtered off. The powder was added to 10 ml of 80% formic acid and heated for 30 minutes at 50° C. The solvent was dried under reduced pressure and isopropyl ether was added to the residue to form a powder. The powder was applied to a column chromatography using Diaion HP 20 (trade name) for purification to provide 150 mg of 7β-[2-(2-aminothiazol-4-yl)-3-hydroxypropionamido]-7α-methoxy-3-(1-methyltetrazol-5-yl)thiomethyl-Δ³-cephem-4-carboxylic acid.

(i) Infrared absorption spectra (cm$^{-1}$, KBr): 1765 (lactum), 1670 (amide).
(ii) Nuclear magnetic resonance spectra (d$_6$-DMSO) ppm:

6.23 (1H 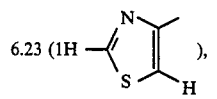), 5.05 (1H 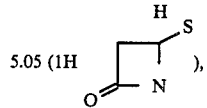), 4.23 (2H 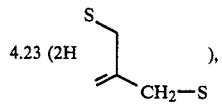), 3.90 (3H 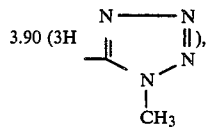), 3.77 (3H —CH—),
         |
         CH$_2$O 3.64 (2H 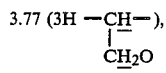), 3.38 (3H 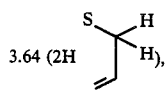).

EXAMPLE 6

In 20 ml of anhydrous tetrahydrofuran were dissolved 430 mg (1 millimole) of 3-hydroxy-2-(2-tritylaminothiazol-4-yl)propionic acid, 510 mg (1 millimole) of 7β-amino-3-(5-methyl-1,3,4-thiadiazol-2-yl)thiomethyl-Δ$^3$-cephem-4-carboxylic acid benzhydryl ester, and after adding thereto 206 mg (1 millimole) of N,N'-dicyclohexylcarbodiimide, the mixture was stirred for 3 hours at room temperature. The reaction mixture was concentrated under reduced pressure and then 40 ml of ethyl acetate was added to the residue. Insoluble N,N'-dicyclohexylurea formed was filtered off and the filtrate was washed with a diluted aqueous acid solution and an aqueous solution of sodium hydrogencarbonate and dried by anhydrous magnesium sulfate. The solvent was distilled off under reduced pressure and then, the residue was treated with ether to form a powder, which was recovered by filtration, and washed with water to provide 720 mg of 7β-[3-hydroxy-2-(tritylaminothiazol-4-yl)propionamido]-3-(5-methyl-1,3,4-thiadiazol-2-yl)thiomethyl-Δ$^3$-cephem-4-carboxylic acid benzhydryl ester.

The product was dissolved in a mixture of 15 ml of trifluoroacetic acid and 1 ml of anisole followed by stirring for 10 minutes at room temperature. After further adding 10 ml of water to the mixture at temperatures below room temperature, the resultant mixture was stirred for 30 minutes at room temperature.

The reaction mixture was concentrated under reduced pressure, ether was added to the residue and the wall of the container was rubbed to form a powder, which was recovered by filtration and washed with ether. The powder was suspended in 10 ml of isopropanol and after adding pyridine to the suspension and adjusting the pH to 4, the mixture was stirred for 30 minutes at room temperature. The powder was then recovered by filtration and washed with isopropanol to provide crude 7β-[2-(2-aminothiazol-4-yl)-3-hydroxypropionamido]-3-(5-methyl-1,3,4-thiadiazol-2yl)thiomethyl-Δ$^3$-cephem-4carboxylic acid. The product was purified by a column chromatography using Diaion HP 20 (trade name) to provide a pure product.

(i) Infrared absorption spectrum (cm$^{-1}$, KBr): 1770 (lactam).
(ii) Nuclear magnetic resonance spectra (D$_6$-DMSO) ppm:

2.65 (3H 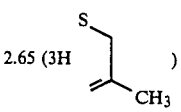)

3.74 (5H —CH—, 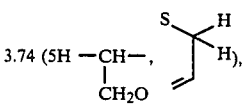),
         |
         CH$_2$O 4.34 (2H 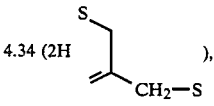), 5.07 (1H 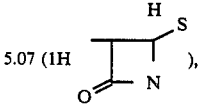), 5.64 (1H 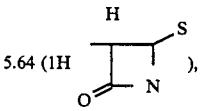), 6.45 (1H 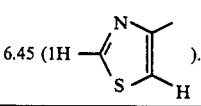).

EXAMPLE 7

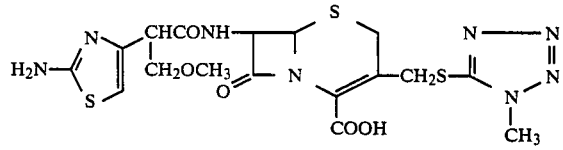

In 45 ml of dichloromethane was dissolved 1.3 g of methyl 3-hydroxy-2-(2-tritylaminothiazol-4-yl)propionate and after adding thereto 0.8 ml of a solution of 0.108 millimole of tetrafluoroboric acid in a mixture of ether and dichloromethane and then 90 ml of an ether solution of diazomethane. The reaction mixture was then reacted for 2 hours.

The reaction mixture was concentrated and after adding ice-water to the concentrate, the product was extracted using ethyl acetate. The ethyl acetate extract was concentrated and applied to a silica gel column chromatography using a mixture of benzene and ethyl acetate in 9:1 by volume ratio to provide methyl 3-methoxy-2-(2-tritylaminothiazol-4-yl)propionate.

Nuclear magnetic resonance spectra (d₆-DMSO)
ppm:   3.08 (3H, s, —OCH₃),
       3.45 (3H, s, —CO₂CH₃), 3.1–3.6 (3H, m, —CH—),
                     |
                     CH₂

6.24 (1H, s, 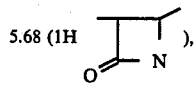).

The ester was dissolved in 30 ml of methanol, 3 ml of an aqueous 25% sodium hydroxide solution was then added, the mixture was heated to 50° C. for 15 minutes to cause hydrolysis and to provide the free acid of the product.

Nuclear magnetic resonance spectra (d₆-DMSO)
ppm:   3.13 (3H, s, —OCH₃), 3.2–3.6 (3H, m, —CH—),
                     |
                     CH₂

6.31 (1H, s, 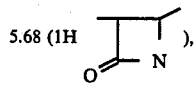).

In 20 ml of dichloromethane were dissolved 444 mg of 3-methoxy-2-(2-tritylaminothiazol-4-yl)propionic acid and 494 mg of benzhydryl 7β-amino-3-(1-methyltetrazol-5-yl)thiomethyl-Δ³-cephem-4-carboxylate and after adding thereto 206 mg of N,N'-dicyclohexylcarbodiimide to cause a reaction, the reaction mixture was treated as usual to provide 3-(1-methyltetrazol-5-yl)thiomethyl-7β-[2-(2-tritylaminothiazol-4-yl)-3-methoxypropionamido]-Δ³-cephem-4-carboxylic acid benzhydryl ester.

(i) Infrared absorption spectra (cm⁻¹, KBr):
    1775, 1715, 1675.
(ii) Nuclear magnetic resonance spectra (d₆-DMSO)
ppm:   3.10 (3H, s, OCH₃), 3.71 (2H, 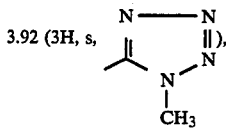), 3,87 (3H, s, 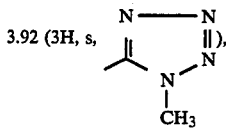), 4.23 (2H, q, —CH₂S—), 5.06 (1H, d, 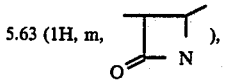), 5.68 (1H 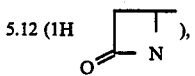), 6.13, 6.19 (1H, 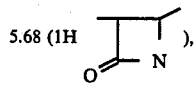).

The product thus obtained was treated with a mixture of trifluoroacetic acid and 70% formic acid to release the protective group to provide 7β-[2-(2-aminothiazol-4-yl)-3-methoxypropionamido]-3-(1-methyltetrazol-5-yl)thiomethyl-Δ³-cephem-4-carboxylic acid.

(i) Infrared absorption spectrum (cm⁻¹, KBr):
    1765.
(ii) Nuclear magnetic resonance spectra (d₆-DMSO)
ppm:   3.24 (3H, s, —OCH₃), 3.92 (3H, s, 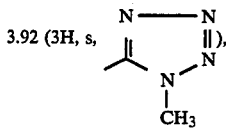), 5.12 (1H 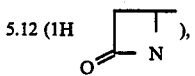), 5.63 (1H, m, 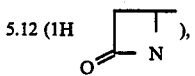), 6.4 (1H 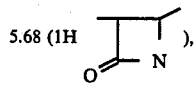)

EXAMPLE 8

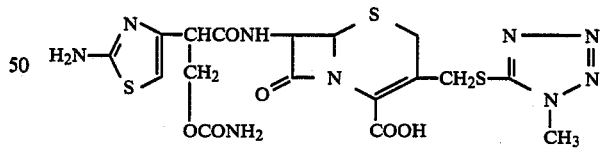

In 20 ml of dichloromethane was dissolved benzhydryl 7β-[3-hydroxy-2-(2-tritylaminothiazol-4-yl)propionamido]-3-(1-methyltetrazol-5-yl)thiomethyl-Δ³-cephem-4-carboxylate and then 0.2 ml of trichloroacetyl isocyanate was added to the solution at 10° C. to cause a reaction for 20 minutes. The reaction mixture was washed with water and dried by anhydrous magnesium sulfate. The solvent was distilled off, the residue was applied to a column chromatography using 30 g of silicagel and the product was eluted with a mixture of benzene and ethyl acetate in 3:1 by volume ratio. The resulting fractions were collected and concentrated to provide 400 mg of 3-(1-methyltetrazol-5-yl)thiomethyl-7β-[3-trichloroacetylcarbamoyloxy-2-(2-tritylaminothiazol-4-yl)propionamido]-Δ³-cephem-4-carboxylic acid benzhydryl ester.

(i) Infrared absorption spectra (cm⁻¹, KBr): 1780, 1715, 1670.
(ii) Nuclear magnetic resonance spectra (CDCl₃)

ppm:

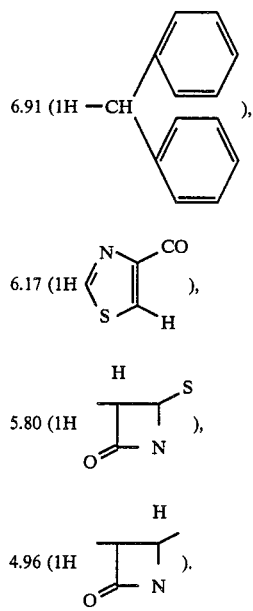

By treating the N-trichloroacetylcarbamoyl compound by a conventional procedure to release the protective group, 7β-[2-(2-aminothiazol-4-yl)-3-carbamoyloxypropionamido]-3-(1-methyltetrazol-5-yl)thiomethyl-Δ³-cephem-4-carboxylic acid was obtained.

(i) Infrared absorption spectra (cm⁻¹, KBr): 1775, 1660.
(ii) Nuclear magnetic resonance spectra (d₆-DMSO)

ppm:

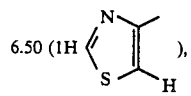

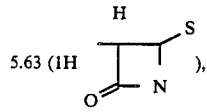

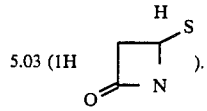

EXAMPLE 9

Product of Example 2: 250 g
Corn starch: 50 g
Talc: 5 g
Silicic anhydride: 1.5 g The above mixture was finely pulverized and filled in 1,000 capsules.

What is claimed is:
1. 7β-[2-(2-aminothiazol-4-yl)-3-carbamoyloxypropionamido]-3-(1-methyltetrazol-5-yl)thiomethyl-3-cephem-4-carboxylic acid.
2. A pharmaceutical composition which exhibits antibacterial activity against both gram negative and gram positive bacteria, and which contains an antibacterially effective amount of the compound of the compound of claim 1 and a pharmaceutically acceptable carrier.
3. A method of treating bacterial infection in a warm blooded animal comprising administering an effective amount of the composition of claim 2 to said warm blooded animal.

* * * * *